US00PP16272P3

(12) United States Plant Patent
Eremin

(10) Patent No.: US PP16,272 P3
(45) Date of Patent: Feb. 21, 2006

(54) *PRUNUS* ROOTSTOCK NAMED 'AP-1'

(50) Latin Name: *Prunus cerasifera×Prunus persica*
Varietal Denomination: AP-1

(75) Inventor: Gennadiy Eremin, Krasnodar (RU)

(73) Assignee: Varieties International, LLC, Lafayette, OR (US)

( * ) Notice: Subject to any disclaimer, the term of this patent is extended or adjusted under 35 U.S.C. 154(b) by 113 days.

(21) Appl. No.: 10/802,611

(22) Filed: Mar. 17, 2004

(65) Prior Publication Data

US 2005/0210553 P1 Sep. 22, 2005

(51) Int. Cl.
*A01H 5/00* (2006.01)

(52) U.S. Cl. ..... Plt./180

(58) Field of Classification Search ..... Plt./183, Plt./180
See application file for complete search history.

(56) References Cited

U.S. PATENT DOCUMENTS

| | | | | | |
|---|---|---|---|---|---|
| PP8,912 | P | * | 9/1994 | Zaiger et al. | Plt./194 |
| PP11,403 | P | * | 6/2000 | Doyle et al. | Plt./184 |
| PP14,126 | P3 | * | 9/2003 | Zaiger et al. | Plt./183 |
| 2002/0138884 | P1 | * | 9/2002 | Zaiger et al. | Plt./180 |
| 2003/0233691 | P1 | * | 12/2003 | Eremin | Plt./180 |

* cited by examiner

*Primary Examiner*—Kent Bell
*Assistant Examiner*—W. C. Haas
(74) *Attorney, Agent, or Firm*—The Webb Law Firm

(57) ABSTRACT

A new and distinct *Prunus cerasifera×Prunus persica* plant used as a rootstock for many different varieties that exhibits desirable propagation characteristics and light pink flowers.

3 Drawing Sheets

Botanical classification: *Prunus cerasifera×Prunus persica.*
Varietal denomination: 'AP-1'.

BACKGROUND OF THE INVENTION

The present invention comprises a new and distinct cultivar of *Prunus cerasifera×Prunus persica* used as a rootstock known by the varietal name 'AP-1'. The new variety was discovered in the Krasnodar region of Russia around 1986. The new variety is the result of planned breeding between a *Prunus cerasifera* plant (female parent) and a *Prunus persica* plant (male parent). The new variety differs from its parents in that its flowers are big and light pink, it is not fruit bearing; 'AP-1' has wide elliptical leaves, and it has serrated leaf margins. The purpose of breeding 'AP-1' was to provide a productive clonal rootstock for peach and plum varieties. The new variety has been trial and field tested and has been found to retain its distinctive characteristics and remain true to type through successive propagations. The following characteristics distinguish 'AP-1' from other varieties known to the breeder:

1. 'AP-1' may be propagated via hardwood or softwood cuttings;
2. 'AP-1' has a strong root system;
3. 'AP-1' is resistant to nematodes, chlorosis, *Cytospora,* and *Verticillium;* and
4. 'AP-1' is drought resistant.

DESCRIPTION OF THE DRAWINGS

The accompanying photographic drawings illustrate the new variety, with the color being as nearly true as is possible with color illustrations of this type.

DETAILED BOTANICAL DESCRIPTION

Figure 1:
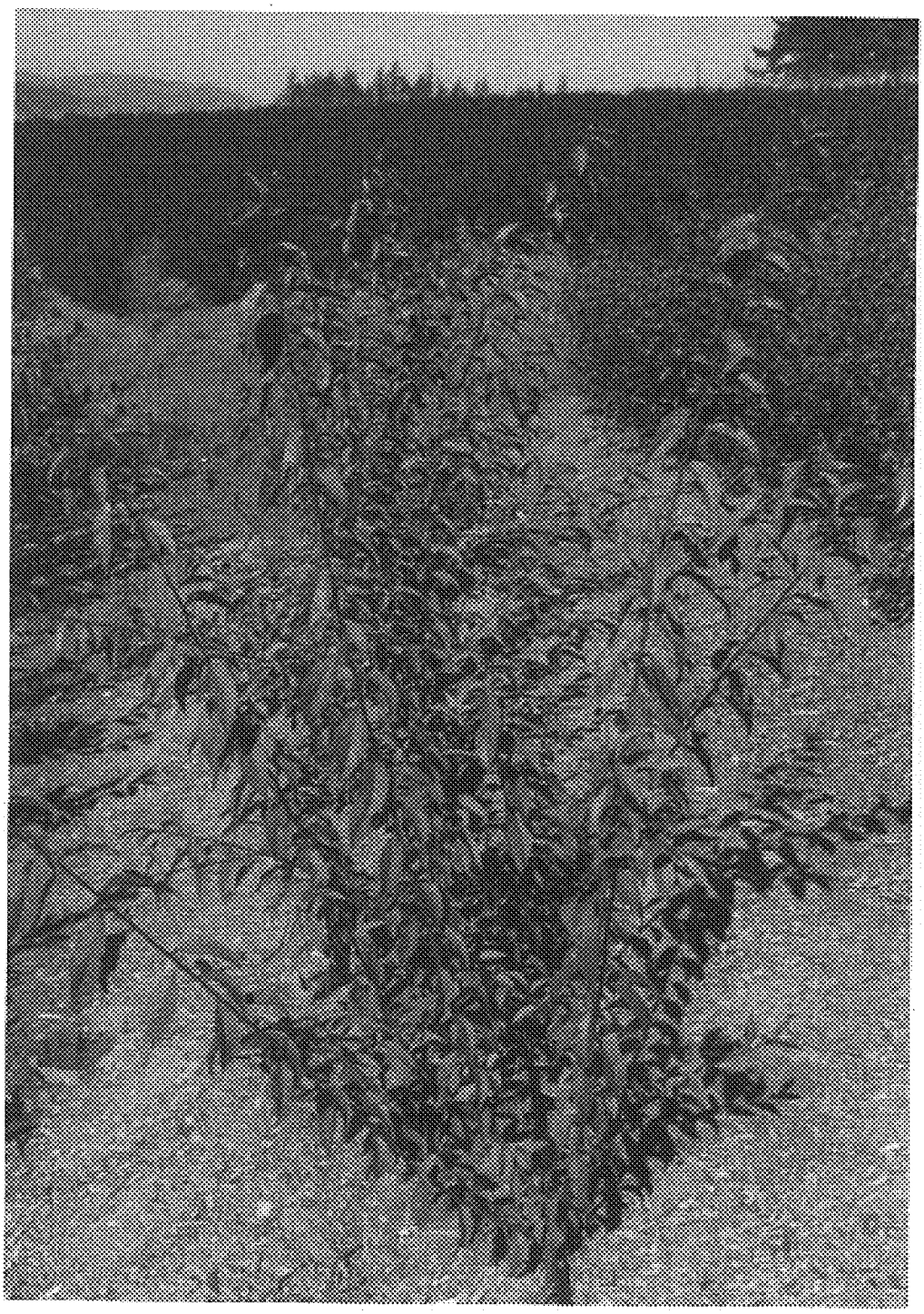
FIG. 1 shows the new variety grown to a flowering plant.
Figure 2:
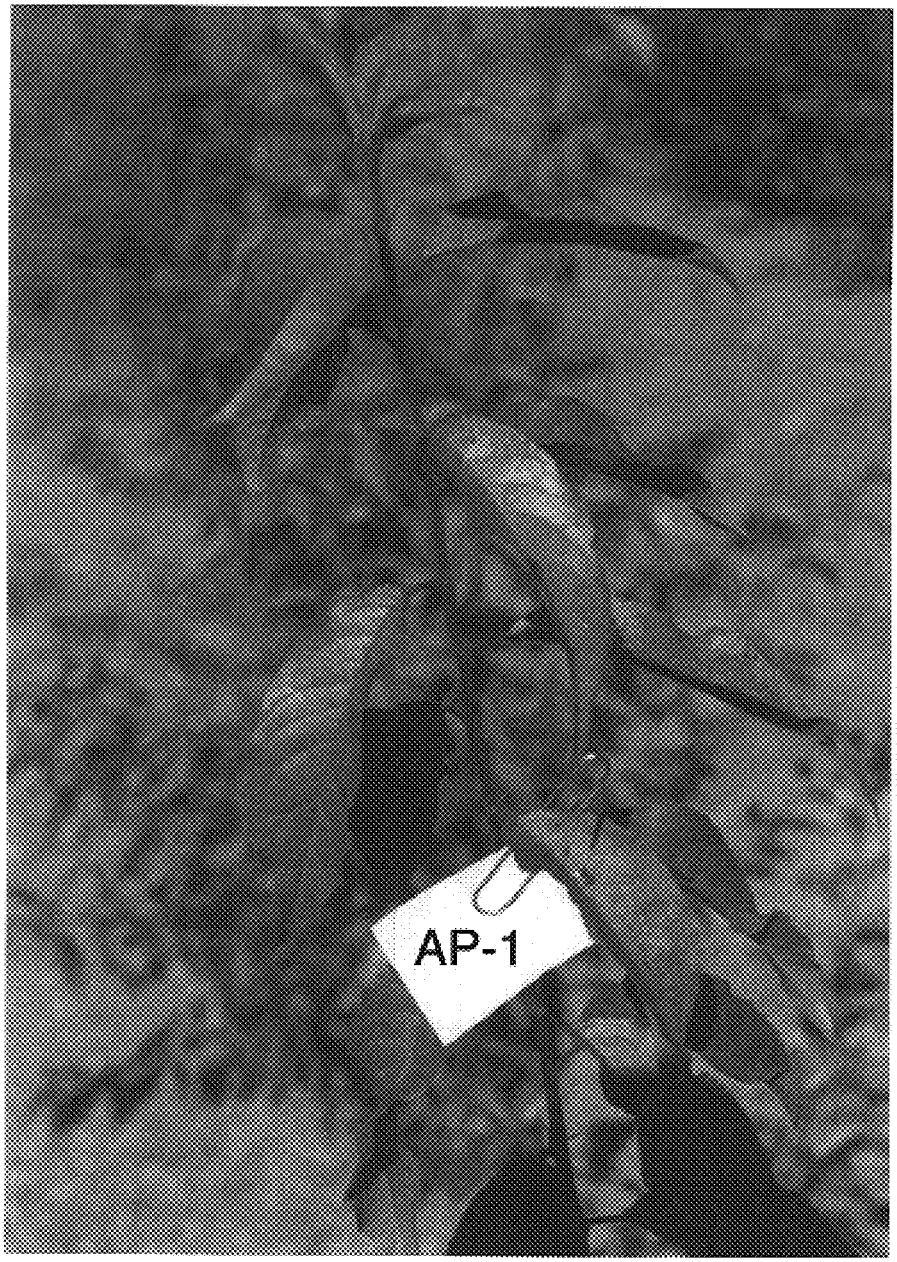
FIG. 2 shows a close-up view of leaves of the new variety.
Figure 3:
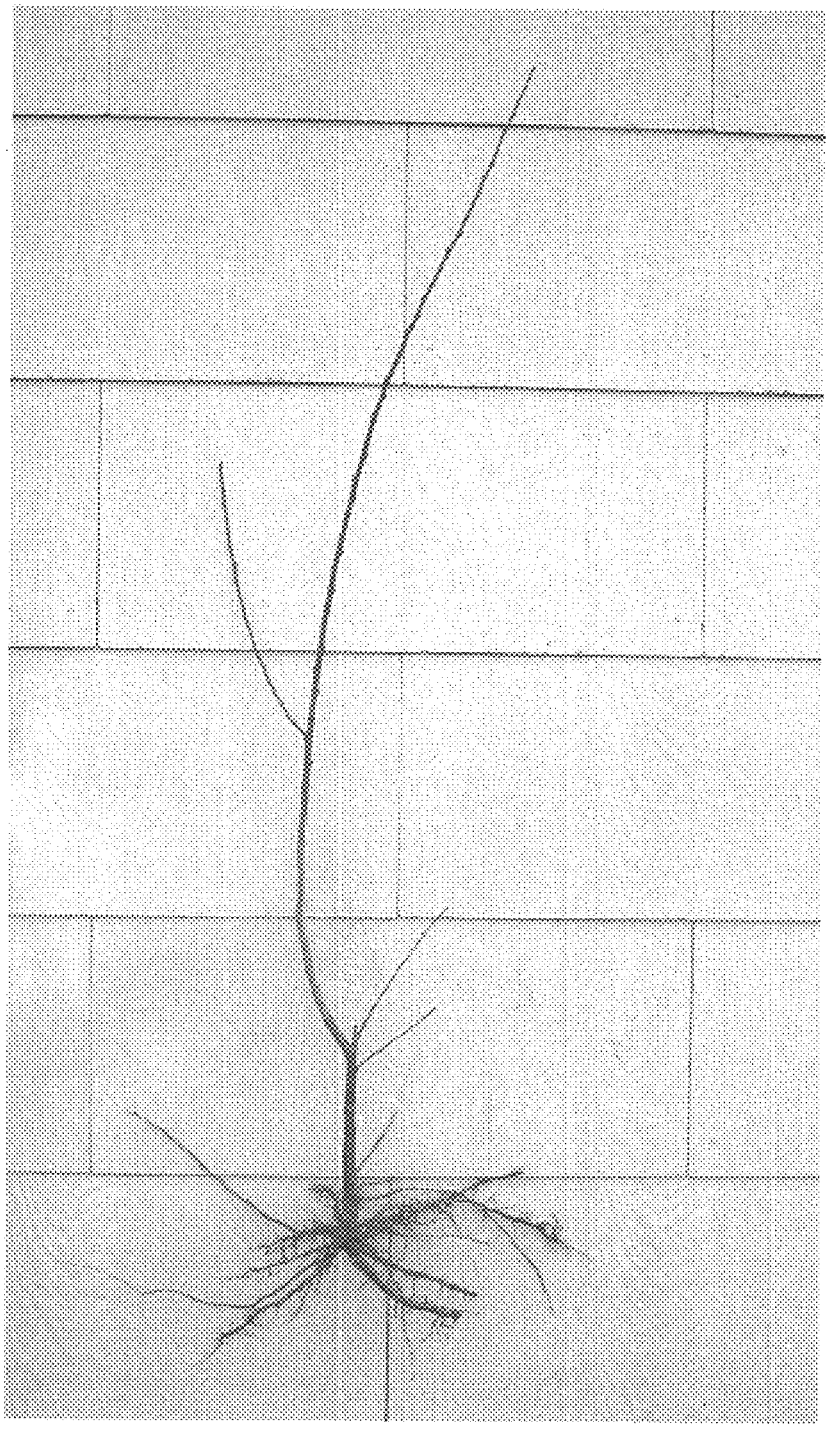
FIG. 3 illustrates the roots and branches of the new variety.

The following detailed description sets forth the characteristics of the new cultivar. The data which defines these characteristics were collected from plants produced by asexual reproductions via cuttings, and grown on their own roots, carried out in the Krasnodar Region of Russia. The new variety was grown under warm, dry Summer conditions with a temperature range of 70° F. to 105° F. The Winter months are mild with lows to −10° F. The Spring and Fall months are humid. The color readings were taken in natural daylight.

Tree:
Use: Rootstock.
Fruit bearing: No fruit observed to date on 'AP-1'.
Size (generally): Medium.
*Height at 2 years.*—3 feet.
*Spread at 2 years.*—1.5 feet.
Form: Rounded; spreading.
Trunk:
*Size.*—Medium.
*Bark color.*—177A.
*Surface texture.*—Smooth or with very weak pubescence.
*Diameter.*—9.0 mm at 3 years when grown in a pot.
*Texture.*—Smooth.
*Lenticel number.*—7 to 12 per $cm^2$ at 3 years.

Branches:
*Surface texture.*—Smooth.
*Young bark color.*—178B.
*Mature bark color.*—179A.
*Internode length.*—2.0 cm to 2.5 cm.
*Lenticel size.*—3.0 mm×1.0 mm, when observed.
*Lenticel number.*—Few; none observed on a 1 year old branch.
*Lenticel shape.*—Oval.
*Leaf bud shape.*—Conical.
*Leaf bud size.*—3.0 mm.
*Leaf bud texture.*—Pubescent.
*Branch diameter.*—5.0 mm at 1 year.
*Crotch angle.*—60°.
Leaves:
*Bud.*—Length: 1.5 mm. Diameter: 1.5 mm. Color: 171A.
*Length.*—14.0 cm.
*Width.*—5.0 cm.
*Surface texture.*—Upper surface is glossy.
*Form.*—Narrow; elliptic.
*Color.*—Both surfaces: About 137A to 138A (Upper surface, occasional reddish tinge toward margin.).
*Mid-vein.*—Size: Thin. Color: White, with the center being light pink.
*Petiole.*—Length: 1.0 cm. Thickness: 1.5 mm to 2.0 mm. Color: Pink About 178B to 179A.
*Leaf glands.*—Absent.
*Stipules.*—Size: Up to 2.0 cm. Color: Green.
Flowers:
*Bloom time.*—Flowers reach full bloom the third week of March.
*Size.*—35.0 mm to 38.0 mm.
*Color.*—Light pink.
Number.—1 to 3 flowers per flower bud.
*Fragrance.*—None.
*Petals.*—Number: 5 per flower. Shape: Broadly obovate. Length: 20.0 mm. Width: Widest point is 18.0 mm; the base and apex are both 15.0 mm. Texture: Smooth. Color: 62D. Appearance: Petals overlap at full bloom.
Sepals:
*Number.*—5 per bloom.
*Shape.*—Ovoid to round.
*Length.*—4.0 mm.
*Width.*—3.0 mm.
*Color.*—138C in the middle.
Reproductive organs:
*Anthers.*—Number: 34 to 40. Color: 17B. Filament length: 13.0 mm. Filament color: 62C.
*Stigma.*—Number: 1. Position: Below the anthers.
*Style.*—Length: 4.0 mm. Color: 130D.
Fruit: None observed to date.
Soil adaptation and tolerance:
Chlorosis: 'AP-1' is resistant to high pH and lime which causes lime-induced chlorosis.
Wet soil: Resilient.
Cold temperatures: Hardy to Zone 4.
Asphixia: Resistant; will survive water-logged soil for extended time periods.
Multiplication ability:
Layering: None.
Hardwood cuttings: Great propagation.
Softwood cuttings: Great propagation.
Pathogen resistance:
Fungal disease: Resistant to all fungi exposed to the new variety.
Insects: Not resistant.
Mites: Weak resistance.
Viruses: Resistant.
Diseases: Resistant to *Cytospora, Verticillium,* and bacterial canker.
Root-knot nematodes: Immune, according to three tests in Spain.
Lesion nematodes: Highly resistant.
Performance as a rootstock when grafted:
Root sprouts (suckering): Suckers (shoots that grow from the rootstock and disrupt the growth of the scion) are not present.
Anchorage: Very good.
Compatibility: Good compatibility with all varieties of peaches, almonds, nectarines, Japanese plums, Russian plums, and apricots known to the breeder.
Vigor: Medium to strong.

I claim:

1. A new and distinct variety of *Prunus cerasifera*×*Prunus persica* plant, as illustrated and described.

* * * * *